(12) United States Patent
Hjelmgaard et al.

(10) Patent No.: US 11,590,747 B2
(45) Date of Patent: Feb. 28, 2023

(54) METHOD OF PRODUCING A MINERAL WOOL PRODUCT COMPRISING A MULTIPLE OF LAMELLAE AND A PRODUCT OF SUCH KIND

(71) Applicant: Rockwool International A/S, Hedehusene (DK)

(72) Inventors: Thomas Hjelmgaard, Fredensborg (DK); Oskar Meres, Vallensbæk Strand (DK); Bent Jacobsen, Lejre (DK)

(73) Assignee: Rockwool International A/S, Hedehusene (DK)

( * ) Notice: Subject to any disclaimer, the term of this patent is extended or adjusted under 35 U.S.C. 154(b) by 77 days.

(21) Appl. No.: 16/301,232

(22) PCT Filed: May 11, 2017

(86) PCT No.: PCT/EP2017/061410
§ 371 (c)(1),
(2) Date: Nov. 13, 2018

(87) PCT Pub. No.: WO2017/194717
PCT Pub. Date: Nov. 16, 2017

(65) Prior Publication Data
US 2019/0210323 A1   Jul. 11, 2019

(30) Foreign Application Priority Data

May 13, 2016 (EP) .................................. 16169635
May 13, 2016 (EP) .................................. 16169638
May 13, 2016 (EP) .................................. 16169641

(51) Int. Cl.
*B32B 37/12* (2006.01)
*C09J 101/28* (2006.01)
(Continued)

(52) U.S. Cl.
CPC ............... *B32B 37/12* (2013.01); *B32B 5/12* (2013.01); *B32B 5/26* (2013.01); *B32B 7/12* (2013.01);
(Continued)

(58) Field of Classification Search
CPC ..... B32B 37/12; B32B 37/18; B32B 38/0004; B32B 2037/1253; B32B 2250/20;
(Continued)

(56) References Cited

U.S. PATENT DOCUMENTS 3,411,972 A   11/1968   Salyer et al.
4,040,213 A   8/1977    Capaul
(Continued)

FOREIGN PATENT DOCUMENTS

CN   101302410 A   11/2008
CN   102068008 A   5/2011
(Continued)

OTHER PUBLICATIONS

Machine Translation of EP-0560878-B1, Oct. 1994 (Year: 1994).*
(Continued)

*Primary Examiner* — John L Goff, II
(74) *Attorney, Agent, or Firm* — Dinsmore & Shohl LLP

(57) ABSTRACT

A method and a mineral wool product include a multiple of lamellae, such as a sandwich panel core. The product includes a plurality of lamellae cut from a mineral wool web, and bonded together by applying an adhesive on the surfaces of two adjacent lamellae to form a web-like product, wherein the adhesive comprises at least one hydrocolloid.

31 Claims, 1 Drawing Sheet

Figure 1:
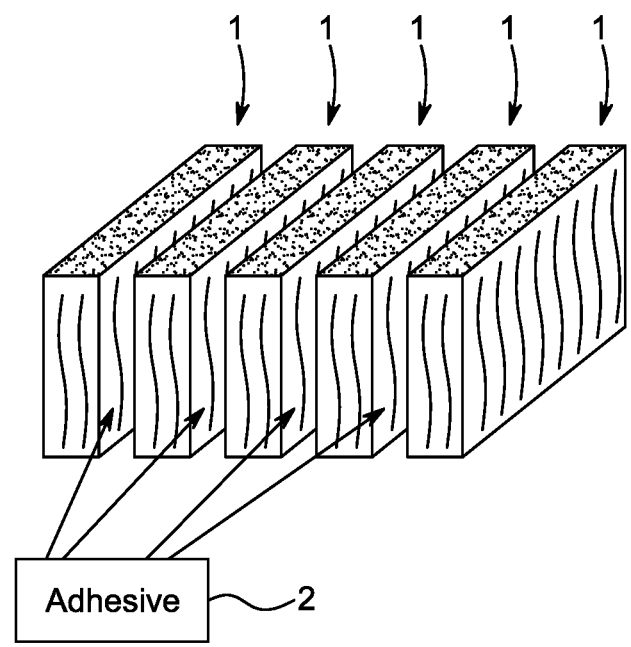

(51) Int. Cl.
| | |
|---|---|
| C09J 103/02 | (2006.01) |
| C09J 105/04 | (2006.01) |
| C09J 105/06 | (2006.01) |
| C09J 189/06 | (2006.01) |
| D04H 1/4218 | (2012.01) |
| D04H 1/74 | (2006.01) |
| C09J 105/12 | (2006.01) |
| B32B 5/12 | (2006.01) |
| B32B 5/26 | (2006.01) |
| C08L 5/12 | (2006.01) |
| C03C 25/26 | (2018.01) |
| B32B 19/04 | (2006.01) |
| B32B 15/14 | (2006.01) |
| C09J 105/00 | (2006.01) |
| B32B 37/14 | (2006.01) |
| D04H 1/413 | (2012.01) |
| D04H 1/64 | (2012.01) |
| D04H 3/002 | (2012.01) |
| E04B 1/94 | (2006.01) |
| C03C 13/06 | (2006.01) |
| C08L 1/28 | (2006.01) |
| C08L 3/02 | (2006.01) |
| D04H 3/004 | (2012.01) |
| E04B 1/88 | (2006.01) |
| C09J 189/00 | (2006.01) |
| C08J 5/04 | (2006.01) |
| C03C 25/32 | (2018.01) |
| C09J 11/06 | (2006.01) |
| D04H 1/587 | (2012.01) |
| E04B 1/74 | (2006.01) |
| C08L 89/06 | (2006.01) |
| D04H 1/4266 | (2012.01) |
| D04H 1/724 | (2012.01) |
| B32B 7/12 | (2006.01) |
| B32B 37/18 | (2006.01) |
| B32B 38/00 | (2006.01) |
| C03C 25/321 | (2018.01) |
| C03C 25/328 | (2018.01) |
| C09J 5/00 | (2006.01) |
| D04H 1/4209 | (2012.01) |
| D04H 1/593 | (2012.01) |
| E04B 1/80 | (2006.01) |
| E04C 2/284 | (2006.01) |
| E04D 3/35 | (2006.01) |
| E04F 13/08 | (2006.01) |
| E04B 1/76 | (2006.01) |
| C12N 9/06 | (2006.01) |
| C12N 9/02 | (2006.01) |
| C12N 9/08 | (2006.01) |
| C12N 9/10 | (2006.01) |
| C12N 9/90 | (2006.01) |

(52) U.S. Cl.
CPC ............ *B32B 15/14* (2013.01); *B32B 19/04* (2013.01); *B32B 19/041* (2013.01); *B32B 37/1207* (2013.01); *B32B 37/146* (2013.01); *B32B 37/18* (2013.01); *B32B 38/0004* (2013.01); *C03C 13/06* (2013.01); *C03C 25/26* (2013.01); *C03C 25/32* (2013.01); *C03C 25/321* (2013.01); *C03C 25/328* (2013.01); *C08J 5/043* (2013.01); *C08L 1/286* (2013.01); *C08L 3/02* (2013.01); *C08L 5/12* (2013.01); *C08L 89/06* (2013.01); *C09H 11/00* (2013.01); *C09J 5/00* (2013.01); *C09J 11/06* (2013.01); *C09J 101/28* (2013.01); *C09J 101/286* (2013.01); *C09J 103/02* (2013.01); *C09J 105/00* (2013.01); *C09J 105/04* (2013.01); *C09J 105/06* (2013.01); *C09J 105/12* (2013.01); *C09J 189/005* (2013.01); *C09J 189/06* (2013.01); *D04H 1/413* (2013.01); *D04H 1/4209* (2013.01); *D04H 1/4218* (2013.01); *D04H 1/4266* (2013.01); *D04H 1/587* (2013.01); *D04H 1/593* (2013.01); *D04H 1/64* (2013.01); *D04H 1/724* (2013.01); *D04H 1/74* (2013.01); *D04H 3/002* (2013.01); *D04H 3/004* (2013.01); *E04B 1/74* (2013.01); *E04B 1/80* (2013.01); *E04B 1/88* (2013.01); *E04B 1/94* (2013.01); *E04C 2/284* (2013.01); *E04D 3/352* (2013.01); *E04F 13/0866* (2013.01); *B32B 38/164* (2013.01); *B32B 2037/1215* (2013.01); *B32B 2037/1253* (2013.01); *B32B 2037/1269* (2013.01); *B32B 2250/20* (2013.01); *B32B 2250/40* (2013.01); *B32B 2255/02* (2013.01); *B32B 2255/26* (2013.01); *B32B 2262/108* (2013.01); *B32B 2305/20* (2013.01); *B32B 2305/72* (2013.01); *B32B 2307/304* (2013.01); *B32B 2307/732* (2013.01); *B32B 2309/02* (2013.01); *B32B 2315/14* (2013.01); *B32B 2317/00* (2013.01); *B32B 2419/06* (2013.01); *B32B 2607/00* (2013.01); *C03C 2213/00* (2013.01); *C03C 2218/11* (2013.01); *C08J 2301/28* (2013.01); *C08J 2303/02* (2013.01); *C08J 2389/06* (2013.01); *C08J 2405/00* (2013.01); *C08J 2405/04* (2013.01); *C08J 2405/06* (2013.01); *C08J 2405/12* (2013.01); *C08J 2491/00* (2013.01); *C08J 2493/00* (2013.01); *C08L 2201/52* (2013.01); *C08L 2205/03* (2013.01); *C09J 2400/146* (2013.01); *C09J 2401/00* (2013.01); *C09J 2403/00* (2013.01); *C09J 2405/00* (2013.01); *C09J 2489/00* (2013.01); *C12N 9/0022* (2013.01); *C12N 9/0051* (2013.01); *C12N 9/0059* (2013.01); *C12N 9/0065* (2013.01); *C12N 9/0071* (2013.01); *C12N 9/1044* (2013.01); *C12N 9/90* (2013.01); *C12Y 104/03013* (2013.01); *C12Y 108/03002* (2013.01); *C12Y 110/03001* (2013.01); *C12Y 111/01007* (2013.01); *C12Y 114/18001* (2013.01); *C12Y 203/01013* (2013.01); *C12Y 203/02013* (2013.01); *C12Y 503/04001* (2013.01); *D10B 2505/20* (2013.01); *E04B 2001/742* (2013.01); *E04B 2001/743* (2013.01); *E04B 2001/745* (2013.01); *E04B 2001/7683* (2013.01)

(58) Field of Classification Search
CPC ....... B32B 2315/14; C09J 5/00; C09J 189/00; C09J 189/06; C09J 2401/00; C09J 2403/00; C09J 2405/00; C09J 2489/00; C09J 101/28; C09J 103/02; D04H 1/4266; D04H 1/4209; D04H 1/593; D04H 1/74
See application file for complete search history.

(56) References Cited

U.S. PATENT DOCUMENTS

| | | |
|---|---|---|
| 4,283,457 A | 8/1981 | Kolsky et al. |
| 4,552,793 A | 11/1985 | Cameron et al. |
| 5,100,802 A | 3/1992 | Mickols |
| 5,298,205 A | 3/1994 | Hayes et al. |
| 5,430,070 A | 7/1995 | Kono |

(56) References Cited

U.S. PATENT DOCUMENTS

| | | |
|---|---|---|
| 9,163,342 B2 | 10/2015 | Rosenberg et al. |
| 2004/0069770 A1 | 4/2004 | Cary et al. |
| 2004/0192616 A1 | 9/2004 | Kiel et al. |
| 2007/0036975 A1 | 2/2007 | Miele et al. |
| 2007/0142596 A1 | 6/2007 | Swift et al. |
| 2010/0330376 A1* | 12/2010 | Trksak ............... C08J 5/045 |
| | | 428/426 |
| 2011/0003522 A1 | 1/2011 | Chen et al. |
| 2011/0101260 A1 | 5/2011 | Pons Y Moll et al. |
| 2011/0200814 A1 | 8/2011 | Hernandez-Torres et al. |
| 2011/0266488 A1 | 11/2011 | Didier |
| 2012/0319029 A1 | 12/2012 | Jaffrennou et al. |
| 2014/0134497 A1 | 5/2014 | Lester et al. |
| 2017/0121964 A1* | 5/2017 | Wiker ................. E04B 9/067 |

FOREIGN PATENT DOCUMENTS

| | | | | |
|---|---|---|---|---|
| CN | 102575397 A | 7/2012 | | |
| DE | 3223246 A1 | 1/1983 | | |
| DE | 4130077 A1 | 3/1993 | | |
| EA | 014260 B1 | 10/2010 | | |
| EA | 017247 | 11/2012 | | |
| EA | 019897 | 7/2014 | | |
| EP | 0560878 B1 * | 10/1994 | ............... | D04H 1/64 |
| EP | 0708161 A1 | 4/1996 | | |
| EP | 0726317 A2 | 8/1996 | | |
| EP | 0741003 A1 | 11/1996 | | |
| EP | 1020198 A2 | 7/2000 | | |
| EP | 1184033 A1 | 3/2002 | | |
| EP | 1714780 A1 | 10/2006 | | |
| EP | 2738232 A1 * | 6/2014 | ............... | C09J 11/08 |
| EP | 2990494 A1 | 3/2016 | | |
| ES | 1074717 U | 6/2011 | | |
| GB | 1215113 A | 12/1970 | | |
| NL | 1001508 C2 | 5/1997 | | |
| RU | 2017770 C1 | 8/1994 | | |
| RU | 2325419 C1 | 5/2008 | | |
| RU | 2448830 C2 | 4/2012 | | |
| RU | 2488606 C2 | 7/2013 | | |
| RU | 2501825 C2 | 12/2013 | | |
| WO | 8807614 A1 | 10/1988 | | |
| WO | 9210602 A1 | 6/1992 | | |
| WO | 9719141 A1 | 5/1997 | | |
| WO | 9936368 A1 | 7/1999 | | |
| WO | 0105725 A1 | 1/2001 | | |
| WO | 0196460 A2 | 12/2001 | | |
| WO | 0206178 A1 | 1/2002 | | |
| WO | 2004007615 A1 | 1/2004 | | |
| WO | 2005068574 A1 | 7/2005 | | |
| WO | 2006061249 A1 | 6/2006 | | |
| WO | 2007014236 A2 | 2/2007 | | |
| WO | 2008005635 A2 | 1/2008 | | |
| WO | 2008023032 A1 | 2/2008 | | |
| WO | 2008084173 A2 | 7/2008 | | |
| WO | 2009080938 A2 | 7/2009 | | |
| WO | 2010106181 A1 | 9/2010 | | |
| WO | 2010132641 A1 | 11/2010 | | |
| WO | WO-2010125163 A1 * | 11/2010 | ............ | C08L 89/005 |
| WO | 2011002730 A1 | 1/2011 | | |
| WO | 2011044490 A1 | 4/2011 | | |
| WO | 2011138458 A1 | 11/2011 | | |
| WO | 2012010694 A1 | 1/2012 | | |
| WO | 2012013780 A1 | 2/2012 | | |
| WO | 2012098040 A1 | 7/2012 | | |
| WO | 2012118939 A1 | 9/2012 | | |
| WO | 2013179323 A1 | 12/2013 | | |
| WO | 2016005481 A1 | 1/2016 | | |
| WO | 2016102444 A1 | 6/2016 | | |

OTHER PUBLICATIONS

Pena C et al. Enhancing water repellence and mechanical properties of gelatin films by tannin addition; Bioresource Technology 101 (2010) 6836-6842; 7 pages.

Sartuqui Javier et al; Biomimetic fiber mesh scaffolds based on gelatin and hydroxyapatite nano-rods; Designing intrinsic skills to attain bone reparation abilities; contents lists available at Science Direct; pp. 382-391.

Broderick et al.; Enzymatic Stabilization of Gelatin-Based Scaffolds; 2004 Wiley Periodicals, Inc.; pp. 37-42.

Plashchina, Irina L et al; Phase behavior of gelatin in the presence of pectin in water-acid medium; Polymer Bulletin 58, 587-596 (2007) DOI 10.1007/s00289-006-0691-3.

Bae, Ho J et al., Effects of transglutal ninase-induced cross-linking on properties offish gelatin-nanoclay composite film, Food Chemistry 114 (2009) 180-189.

Zitko, V., Reaction of Pectin With Gelatine (?) Composition of Pectin and Gelatine Complexes, Chemical Journals XVI, 6—Bratislava 1962; pp. 474-481.

\* cited by examiner

METHOD OF PRODUCING A MINERAL WOOL PRODUCT COMPRISING A MULTIPLE OF LAMELLAE AND A PRODUCT OF SUCH KIND

CROSS-REFERENCE TO RELATED APPLICATIONS

This application is the U.S. national stage of PCT/EP2017/061410 filed May 11, 2017, which claims priority of European Patent Application 16169635.6 filed May 13, 2016, which claims priority of European Patent Application 16169638.0 filed May 13, 2016, which claims priority of European Patent Application 16169641.4 filed May 13, 2016 each of which is hereby incorporated by reference in its entirety.

FIELD OF THE INVENTION

The present invention relates to a method of producing a mineral wool product comprising a multiple of lamellae and a product of such kind.

BACKGROUND OF THE INVENTION

In some mineral wool products, such as sandwich panel products, the mineral wool product is a so-called sandwich panel core. A sandwich panel core may be made by the general method where a cured mineral wool web is cut longitudinally into elements being lamellae and the lamellae thus formed are turned 90° about their longitudinal axis where after the lamellae thus oriented are bonded together with the adhesive to form a web-like product which is then cut into desired lengths to form board elements. Due to the turning of the lamellae the fibres of the finished boards will predominantly be oriented in a plane perpendicular to the surfaces of the boards and as a result thereof boards having a considerable stiffness and strength perpendicularly to the surfaces of the boards are obtained. An example of such assembly of lamellae and the manufacturing process thereof is known from e.g. WO 2005/068574 A1.

In WO 2005/068574 A1 there is disclosed a method of manufacturing a board using a hot melt adhesive to bond the mineral wool fibre elements together. The elements are bonded together by the hot-melt adhesive, which is cured by heating the bonded structure to a temperature of approx. 150-185° C.

An alternative way of forming the lamellae board is known from DE 32 23 246 A1. In this disclosure the lamellae board is formed by gluing batts together on top of each other and subsequently cut a slice.

When using such lamellae product as a sandwich panel core, the core is provided with metal sheets on major surfaces of the panel to provide a sandwich panel product, such as by adhesion with the adhesive.

The lamellae product may also be used for insulation of facades (e.g. Fasrock XL) or flat roof insulation, where compression strength is an important parameter.

Bonding together or laminating elements is utilized for different purposes respectively to achieve improved insulation, strength, stability, appearance or other properties.

Insulating characteristics of ready-made panels depend among other things upon the way in which individual panels are installed and/or bonded together at a construction site. The bigger the number of small panels necessary to form a requested surface, the bigger the number of edges at which panels are in mutual contact. The bigger the number of contact edges between the panels, the bigger the number of thermal bridges will be formed on the insulated surface as a result of inaccurate laying, improper adjustment of individual panels, and also as a result of increased risk of soiling contact surfaces.

In the past, phenol-formaldehyde resins which can be economically produced have been used as adhesive compositions for bonding together mineral wool elements.

However, these adhesives suffer from the disadvantage that they contain formaldehyde and they are therefore potentially harmful to handle and require protective measures when handling them on-site.

Non-phenol-formaldehyde binders which can be used as adhesives are sugar based binders, such as for example the compositions disclosed in EP2990494A1, PCT/EP2015/080758, WO02007/014236, WO02011/138458 and WO2009/080938.

However, all these binders, when used as adhesives for bonding together the surfaces of mineral wool elements, suffer from the disadvantage that they require high temperatures for curing which makes it necessary to apply heat over a prolonged time to the elements to be bonded together. This does not only require additional equipment but can also cause a fire hazard, e.g. when bonding together isolation elements for a roof insulation on-site. Further, the high temperature curing of these known adhesives can cause the emission of harmful or irritating fumes which may require protective measures for the handling of this matter.

Another type of adhesive that has been used for gluing together mineral wool elements with each other or with other elements such as glass fleece or metal sheet is a polyurethane based adhesive. This may be a one- or two-component adhesive. Such adhesives do not necessarily have to be cured at high temperatures. However, these adhesives may also be harmful when handling and are not based on naturally occurring ingredients.

Other adhesives are based on PVA, bitumen, inorganic binders PUR, and/or polyacrylates.

SUMMARY OF THE INVENTION

Accordingly, it was an object of the present invention to provide a method of producing mineral wool fibre boards comprising a multiple of lamellae, whereby the method uses an adhesive that does not require high temperatures for curing and whereby during the handling, application, and curing of the adhesive exposure to harmful substances is minimized and no protective measures are necessary.

This object is achieved by a method of producing a mineral wool product comprising a multiple of lamellae, said method comprising the steps of:
  providing a cured mineral wool web;
  cutting said mineral wool web into a plurality of lamellae,
  bonding the lamellae together by applying an adhesive on the surfaces of two adjacent lamellae,
  curing the adhesive, wherein the adhesive comprises at least one hydrocolloid.

Producing the mineral wool product by cutting lamellae and bonding the lamellae together is very versatile in production as any number of lamellae may be bonded together, and the mutual position of neighbouring lamellae may be adjusted to form a staggered pattern for making a large mineral wool product, e.g. having a length longer than the individual lamellae. A staggered pattern of the lamellae in the mineral wool product may be advantageous to not have breaking points at the same location across a mineral wool product as such breaking points introduce weaknesses.

According to an alternative embodiment the adhesive is applied to the surface of the cured mineral wool web before cutting the mineral wool web into lamellae. This should be understood to include an embodiment comprising bonding a plurality of mineral wool webs together to form a laminate and cutting slices of the laminate. The slices would then be formed of a plurality of lamellae bonded together. This embodiment may be preferable for producing a standard product of a length, which is the same as or shorter length than the individual lamellae.

This alternative embodiment should also be understood to include an embodiment comprising the consecutive steps of applying adhesive to the cured mineral wool web, cutting the mineral wool web into lamellae, and bonding these lamellae together. This embodiment may have the advantage that it is easier to apply the adhesive to the relatively large surface of the mineral wool web compared to the relatively small surface of the lamellae.

By lamellae is meant that the mineral wool web is cut into strips which are relatively long and thin, such as 1200×200 mm. The lamellae may be cut cross-wise to the web or along the longitudinal axis of the web. Generally the dominant fibre direction in a mineral wool web is a plane more or less parallel to the major surfaces of the web.

By the invention it is found advantageous to use the particular type of adhesive, especially when it has the preferred features set out, as there can be provided particularly durable connections for lamellae.

It is surprisingly found that it is possible to bond together the surfaces of not only mineral wool elements with each other but also one or more another kinds of element, such as metal sheets, by using the method described. It is further advantageous that the adhesive used can be cured at relatively low temperatures. Furthermore, since the adhesive used for the method in some embodiments does usually not contain any harmful substances and does usually not set free any harmful substances during the curing, the method can be carried out by any person on-site of use without any protective measures and without a need for specific training for the persons to carry out the method.

Accordingly, the mineral wool product is preferably a sandwich panel core.

In order to achieve a compression resistant product it is advantageous that the mineral wool web is cut longitudinally into lamellae and the lamellae thus formed are turned 90° about their longitudinal axis where after the lamellae with this orientation are bonded together with the adhesive. This is found advantageous as the fibre orientation of the mineral wool fibre board may be substantially in a plane perpendicular to the surfaces of the mineral wool product after the bonding. The surfaces of the mineral wool product are preferably the surfaces which are intended for facing a building construction or facing away from a construction.

Mineral wool webs are generally produced by collecting fibres produced on a horizontal conveyor, and fibre direction in the mineral wool web produced in this way is generally dominantly horizontal. When such mineral wool webs are cut into lamellae (or elongated strips), which are turned 90° about their longitudinal axis, the main fibre direction of the lamellae will be substantially parallel to a vertical plane.

In a preferred embodiment, the adhesive corresponds with the binder in the mineral wool fibre product. Hereby, a particularly strong bonding is achieved.

According to the method of the invention, the step of curing preferably comprises a drying process, involving blowing air or gas over/through the mineral wool product and/or by increasing temperature. Preferably, the step of curing is carried out at temperatures from 5 to 95° C., such as 10 to 80° C., such as 20 to 60° C., such as 40 to 50° C.

In some preferred embodiment of the invention, the density of the mineral wool fibre product is 50-300 kg/m³, preferably approx. 50-200 kg/m³, more preferably approx. 65-100 kg/m³.

In a second aspect of the invention there is provided a mineral wool product comprising a multiple of lamellae, such as a sandwich panel core, said product comprising
  a plurality of lamellae cut from a mineral wool web, and bonded together by applying an adhesive on the surfaces of two adjacent lamellae to form a web-like product, wherein the adhesive comprises at least one hydrocolloid.

In the product the fibres of the lamellae are predominantly oriented in a plane perpendicular to the major surfaces of the web-like product. The mineral wool fibre product is preferably a cured mineral wool fibre product.

Density of the mineral wool product is a compromise as increasing density increases the strength, but also the cost. In relation to thermal insulation properties optimum densities depends on the materials, fibre diameter etc., but for stone wool insulation the best thermal insulation properties are typically found at densities in the range of 65-80 kg/m³. Suitable density ranges of the mineral wool product is 50-300 kg/m³, preferably approx. 50-200 kg/m³, more preferably approx. 65-100 kg/m³.

DETAILED DESCRIPTION OF PREFERRED EMBODIMENTS

Figure 2:
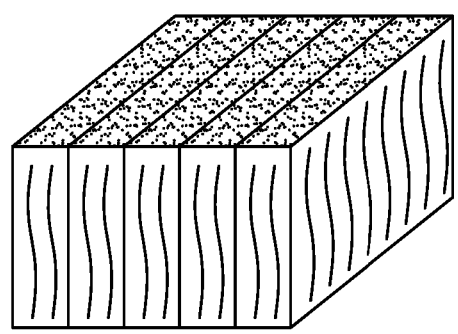

In the following the present invention is described with reference to some preferred embodiments and the accompanying drawings, in which FIG. 1 is a schematic perspective view of a lamellae product prior to the bonding process, and FIG. 2 is the same after the lamellae are bonded together.

A FAÇADE INSULATION PRODUCT

In one embodiment the mineral wool product is a façade insulation product for external insulation of facades, such as an External Thermal Insulation Composite System (ETICS). Such external insulation of buildings is of particular advantage for existing buildings in need of a renovation. Insulation of the building as a whole from the outside is the most efficient way of protection against thermal energy loss, as it fully prevents thermal bridges. Further a render (finish layer or top coat mortar) can be applied directly to the mineral wool providing a visual upgrade of the façade.

A façade insulation product may be made up of for example two lamellae of 1200×200 mm turned 90° about their longitudinal direction and glued together side-by-side to form a board of 1200×400 mm. Thickness may vary depending on the needs, such as from 80 mm to 200 mm. When lamellae are glued together the number of potential thermal bridges between the lamellae are minimized, and the time consumption for mounting the insulation also minimized compared to installation of the individual lamellae.

A Flat Roof Product

In another embodiment the mineral wool product is a flat roof insulation product. Such flat roof insulation products may be made of two or more lamellae glued together in a similar way as described above in relation to the façade insulation product.

A Sandwich Panel Product

With reference to the figures, in one embodiment, the mineral wool product is a so-called sandwich panel core. A sandwich panel core may be made by the general method where a cured mineral wool web is cut longitudinally into elements being lamellae 1 and the lamellae thus formed are turned 90° about their longitudinal axis where after the lamellae thus oriented are bonded together with the adhesive to form a web-like product which is then cut into desired lengths to form board elements. Due to the turning of the lamellae the fibres of the finished boards will predominantly be oriented in a plane perpendicular to the surfaces of the boards and as a result thereof boards having a considerable stiffness and strength perpendicularly to the surfaces of the boards are obtained.

The sandwich panel core is provided with metal sheets (not shown) on major surfaces of the panel to provide a sandwich panel product, such as by adhesion with the adhesive 2.

The adhesive may be applied to the surfaces of the lamellae 1 for instance by spraying or otherwise applied. When a predetermined number of lamellae are aligned the lamellae are bonded together by adjacent surfaces of two neighbouring lamellae contacting each other and then curing the adhesive.

By the invention it is realised that the mineral wool product may also be an uncured mineral wool product, if the lamellae are made of uncured mineral wool.

The Adhesive for Use in the Method of the Present Invention

In one embodiment, the adhesive comprises at least one hydrocolloid.

In one embodiment, the at least one hydrocolloid is selected from the group consisting of gelatine, pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

In one embodiment, the at least one hydrocolloid is a polyelectrolytic hydrocolloid.

In one embodiment, the at least one hydrocolloid is selected from the group consisting of gelatine, pectin, alginate, carrageenan, gum arabic, xanthan gum, cellulose derivatives such as carboxymethylcellulose.

In one embodiment, the adhesive comprises at least two hydrocolloids, wherein one hydrocolloid is gelatine and the at least one other hydrocolloid is selected from the group consisting of pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

Hydrocolloid

Hydrocolloids are hydrophilic polymers, of vegetable, animal, microbial or synthetic origin, that generally contain many hydroxyl groups and may be polyelectrolytes. They are widely used to control the functional properties of aqueous foodstuffs.

Hydrocolloids may be proteins or polysaccharides and are fully or partially soluble in water and are used principally to increase the viscosity of the continuous phase (aqueous phase) i.e. as gelling agent or thickener. They can also be used as emulsifiers since their stabilizing effect on emulsions derives from an increase in viscosity of the aqueous phase.

A hydrocolloid usually consists of mixtures of similar, but not identical molecules and arising from different sources and methods of preparation. The thermal processing and for example, salt content, pH and temperature all affect the physical properties they exhibit. Descriptions of hydrocolloids often present idealised structures but since they are natural products (or derivatives) with structures determined by for example stochastic enzymatic action, not laid down exactly by the genetic code, the structure may vary from the idealised structure.

Many hydrocolloids are polyelectrolytes (for example alginate, gelatine, carboxymethylcellulose and xanthan gum).

Polyelectrolytes are polymers where a significant number of the repeating units bear an electrolyte group. Polycations and polyanions are polyelectrolytes. These groups dissociate in aqueous solutions (water), making the polymers charged. Polyelectrolyte properties are thus similar to both electrolytes (salts) and polymers (high molecular weight compounds) and are sometimes called polysalts.

The charged groups ensure strong hydration, particularly on a per-molecule basis. The presence of counterions and co-ions (ions with the same charge as the polyelectrolyte) introduce complex behavior that is ion-specific.

A proportion of the counterions remain tightly associated with the polyelectrolyte, being trapped in its electrostatic field and so reducing their activity and mobility.

In one embodiment the adhesive comprise one or more counter-ion(s) selected from the group of $Mg^{2+}$, $Ca^{2+}$, $Sr^{2+}$, $Ba^{2+}$.

Another property of a polyelectrolyte is the high linear charge density (number of charged groups per unit length).

Generally neutral hydrocolloids are less soluble whereas polyelectrolytes are more soluble.

Many hydrocolloids also gel. Gels are liquid-water-containing networks showing solid-like behavior with characteristic strength, dependent on their concentration, and hardness and brittleness dependent on the structure of the hydrocolloid(s) present.

Hydrogels are hydrophilic crosslinked polymers that are capable of swelling to absorb and hold vast amounts of water. They are particularly known from their use in sanitary products. Commonly used materials make use of polyacrylates, but hydrogels may be made by crosslinking soluble hydrocolloids to make an insoluble but elastic and hydrophilic polymer.

Examples of hydrocolloids comprise: Agar agar, Alginate, Arabinoxylan, Carrageenan, Carboxymethylcellulose, Cellulose, Curdlan, Gelatine, Gellan, β-Glucan, Guar gum, Gum arabic, Locust bean gum, Pectin, Starch, Xanthan gum. In one embodiment, the at least one hydrocolloid is selected from the group consisting of gelatine, pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

Examples of polyelectrolytic hydrocolloids comprise: gelatine, pectin, alginate, carrageenan, gum arabic, xanthan gum, cellulose derivatives such as carboxymethylcellulose.

In one embodiment, the at least one hydrocolloid is a polyelectrolytic hydrocolloid.

In one embodiment, the at least one hydrocolloid is selected from the group consisting of gelatine, pectin, alginate, carrageenan, gum arabic, xanthan gum, cellulose derivatives such as carboxymethylcellulose.

In one embodiment, the at least one hydrocolloid is a gel former.

In one embodiment, the at least one hydrocolloid is used in form of a salt, such as a salt of $Na^+$, $K^+$, $NH_4^+$, $Mg^{2+}$, $Ca^{2+}$, $Sr^{2+}$, $Ba^{2+}$.

Gelatine

Gelatine is derived from chemical degradation of collagen. Gelatine is water soluble and has a molecular weight of 10,000 to 500,000 g/mol, such as 30,000 to 300,000 g/mol dependent on the grade of hydrolysis. Gelatine is a widely used food product and it is therefore generally accepted that this compound is totally non-toxic and therefore no precautions are to be taken when handling gelatine.

Gelatine is a heterogeneous mixture of single or multi-stranded polypeptides, typically showing helix structures. Specifically, the triple helix of type I collagen extracted from skin and bones, as a source for gelatine, is composed of two $\alpha 1(I)$ and one $\alpha 2(I)$ chains.

Gelatine solutions may undergo coil-helix transitions.

A type gelatins is produced by acidic treatment. B type gelatines are produced by basic treatment.

Chemical cross-links may be introduced to gelatine. In one embodiment, transglutaminase is used to link lysine to glutamine residues; in one embodiment, glutaraldehyde is used to link lysine to lysine, in one embodiment, tannins are used to link lysine residues.

The gelatine can also be further hydrolysed to smaller fragments of down to 3000 g/mol.

On cooling a gelatine solution, collagen like helices may be formed.

Other hydrocolloids may also comprise helix structures such as collagen like helices. Gelatine may form helix structures.

In one embodiment, the cured adhesive comprising hydrocolloid comprises helix structures.

In one embodiment, the at least one hydrocolloid is a low strength gelatine, such as a gelatine having a gel strength of 30 to 125 Bloom.

In one embodiment, the at least one hydrocolloid is a medium strength gelatine, such as a gelatine having a gel strength of 125 to 180 Bloom.

In one embodiment, the at least one hydrocolloid is a high strength gelatine, such as a gelatine having a gel strength of 180 to 300 Bloom.

In a preferred embodiment, the gelatine is preferably originating from one or more sources from the group consisting of mammal, bird species, such as from cow, pig, horse, fowl, and/or from scales, skin of fish.

In one embodiment, urea may be added to the adhesives according to the present invention. The inventors have found that the addition of even small amounts of urea causes denaturation of the gelatin, which can slow down the gelling, which might be desired in some embodiments. The addition of urea might also lead to a softening of the product.

The inventors have found that the carboxylic acid groups in gelatins interact strongly with trivalent and tetravalent ions, for example aluminium salts. This is especially true for type B gelatines which contain more carboxylic acid groups than type A gelatines.

The present inventors have found that in some embodiments, curing/drying of adhesives according to the present invention including gelatin should not start off at very high temperatures.

The inventors have found that starting the curing at low temperatures may lead to stronger products. Without being bound to any particular theory, it is assumed by the inventors that starting curing at high temperatures may lead to an impenetrable outer shell of the adhesive which hinders water from underneath to get out.

Surprisingly, the adhesives according to the present invention including gelatines are very heat resistant. The present inventors have found that in some embodiments the cured adhesives can sustain temperatures up to 300° C. without degradation.

Pectin

Pectin is a heterogeneous grouping of acidic structural polysaccharides, found in fruit and vegetables which form acid-stable gels.

Generally, pectins do not possess exact structures, instead it may contain up to 17 different monosaccharides and over 20 types of different linkages. D-galacturonic acid residues form most of the molecules.

Gel strength increases with increasing $Ca^{2+}$ concentration but reduces with temperature and acidity increase (pH<3).

Pectin may form helix structures.

The gelling ability of the di-cations is similar to that found with alginates ($Mg^{2+}$ is much less than for $Ca^{2+}$, $Sr^{2+}$ being less than for $Ba^{2+}$).

Alginate

Alginates are scaffolding polysaccharides produced by brown seaweeds.

Alginates are linear unbranched polymers containing $\beta$-(1,4)-linked D-mannuronic acid (M) and $\alpha$-(1,4)-linked L-guluronic acid (G) residues. Alginate may also be a bacterial alginate, such as which are additionally O-acetylated. Alginates are not random copolymers but, according to the source algae, consist of blocks of similar and strictly alternating residues (that is, MMMMMM, GGGGGG and GMGMGMGM), each of which have different conformational preferences and behavior. Alginates may be prepared with a wide range of average molecular weights (50-100000 residues). The free carboxylic acids have a water molecule $H_3O^+$ firmly hydrogen bound to carboxylate. $Ca^{2+}$ ions can replace this hydrogen bonding, zipping guluronate, but not mannuronate, chains together stoichiometrically in a so-called egg-box like conformation. Recombinant epimerases with different specificities may be used to produce designer alginates.

Alginate may form helix structures.

Carrageenan

Carrageenan is a collective term for scaffolding polysaccharides prepared by alkaline extraction (and modification) from red seaweed.

Carrageenans are linear polymers of about 25,000 galactose derivatives with regular but imprecise structures, dependent on the source and extraction conditions.

κ-carrageenan (kappa-carrageenan) is produced by alkaline elimination from μ-carrageenan isolated mostly from the tropical seaweed *Kappaphycus alvarezii* (also known as *Eucheuma cottonii*).

ι-carrageenan (iota-carrageenan) is produced by alkaline elimination from ν-carrageenan isolated mostly from the Philippines seaweed *Eucheuma denticulatum* (also called *Spinosum*).

λ-carrageenan (lambda-carrageenan) (isolated mainly from *Gigartina pistillata* or *Chondrus crispus*) is converted into θ-carrageenan (theta-carrageenan) by alkaline elimination, but at a much slower rate than causes the production of ι-carrageenan and κ-carrageenan.

The strongest gels of κ-carrageenan are formed with K+ rather than Li+, Na+, Mg2+, Ca2+, or Sr2+.

All carrageenans may form helix structures.

Gum Arabic

Gum arabic is a complex and variable mixture of arabinogalactan oligosaccharides, polysaccharides and glycoproteins. Gum arabic consists of a mixture of lower relative molecular mass polysaccharide and higher molecular weight hydroxyproline-rich glycoprotein with a wide variability.

Gum arabic has a simultaneous presence of hydrophilic carbohydrate and hydrophobic protein.

Xanthan Gum

Xanthan gum is a microbial desiccation-resistant polymer prepared e.g. by aerobic submerged fermentation from *Xanthomonas campestris*.

Xanthan gum is an anionic polyelectrolyte with a β-(1, 4)-D-glucopyranose glucan (as cellulose) backbone with side chains of-(3,1)-α-linked D-mannopyranose-(2,1)-β-D-glucuronic acid-(4,1)-β-D-mannopyranose on alternating residues.

Xanthan gums natural state has been proposed to be bimolecular antiparallel double helices. A conversion between the ordered double helical conformation and the single more-flexible extended chain may take place at between 40° C.-80° C. Xanthan gums may form helix structures.

Xanthan gums may contain cellulose.

Cellulose Derivatives

An example of a cellulose derivative is carboxymethylcellulose.

Carboxymethylcellulose (CMC) is a chemically modified derivative of cellulose formed by its reaction with alkali and chloroacetic acid.

The CMC structure is based on the β-(1,4)-D-glucopyranose polymer of cellulose. Different preparations may have different degrees of substitution, but it is generally in the range 0.6-0.95 derivatives per monomer unit.

Agar Agar

Agar agar is a scaffolding polysaccharide prepared from the same family of red seaweeds (Rhodophycae) as the carrageenans. It is commercially obtained from species of *Gelidium* and *Gracilariae*.

Agar agar consists of a mixture of agarose and agaropectin. Agarose is a linear polymer, of relative molecular mass (molecular weight) about 120,000, based on the-(1,3)-β-D-galactopyranose-(1,4)-3,6-anhydro-α-L-galactopyranose unit.

Agaropectin is a heterogeneous mixture of smaller molecules that occur in lesser amounts.

Agar agar may form helix structures.

Arabinoxylan

Arabinoxylans are naturally found in the bran of grasses (*Graminiae*).

Arabinoxylans consist of α-L-arabinofuranose residues attached as branch-points to β-(1,4)-linked D-xylopyranose polymeric backbone chains.

Arabinoxylan may form helix structures.

Cellulose

Cellulose is a scaffolding polysaccharide found in plants as microfibrils (2-20 nm diameter and 100-40 000 nm long). Cellulose is mostly prepared from wood pulp. Cellulose is also produced in a highly hydrated form by some bacteria (for example, *Acetobacter xylinum*).

Cellulose is a linear polymer of β-(1,4)-D-glucopyranose units in 4C1 conformation. There are four crystalline forms, Iα, Iβ, II and III.

Cellulose derivatives may be methyl cellulose, hydroxypropyl methylcellulose, hydroxyethyl methylcellulose, hydroxyethyl cellulose, hydroxypropyl cellulose.

Curdlan

Curdlan is a polymer prepared commercially from a mutant strain of *Alcaligenes faecalis* var. *myxogenes*. Curdlan (curdlan gum) is a moderate relative molecular mass, unbranched linear 1,3 β-D glucan with no side-chains.

Curdlan may form helix structures.

Curdlan gum is insoluble in cold water but aqueous suspensions plasticize and briefly dissolve before producing reversible gels on heating to around 55° C. Heating at higher temperatures produces more resilient irreversible gels, which then remain on cooling.

Scleroglucan is also a 1,3 β-D glucan but has additional 1,6 β-links that confer solubility under ambient conditions.

Gellan

Gellan gum is a linear tetrasaccharide 4)-L-rhamnopyranosyl-(α-1,3)-D-glucopyranosyl-(β-1,4)-D-glucuronopyranosyl-(β-1,4)-D-glucopyranosyl-(β-1, with O(2) L-glyceryl and O(6) acetyl substituents on the 3-linked glucose.

Gellan may form helix structures.

β-Glucan

β-Glucans occur in the bran of grasses (*Gramineae*).

β-Glucans consist of linear unbranched polysaccharides of linked β-(1,3)- and β-(1,4)-D-glucopyranose units in a non-repeating but non-random order.

Guar Gum

Guar gum (also called guaran) is a reserve polysaccharide (seed flour) extracted from the seed of the leguminous shrub *Cyamopsis tetragonoloba*.

Guar gum is a galactomannana similar to locust bean gum consisting of a (1,4)-linked β-D-mannopyranose backbone with branch points from their 6-positions linked to α-D-galactose (that is, 1,6-linked-α-D-galactopyranose).

Guar gum is made up of non-ionic polydisperse rod-shaped polymer.

Unlike locust bean gum, it does not form gels.

Locust Bean Gum

Locust bean gum (also called Carob bean gum and Carubin) is a reserve polysaccharide (seed flour) extracted from the seed (kernels) of the carob tree (*Ceratonia siliqua*).

Locust bean gum is a galactomannana similar to guar gum consisting of a (1,4)-linked β-D-mannopyranose backbone with branch points from their 6-positions linked to α-D-galactose (that is, 1,6-linked α-D-galactopyranose).

Locust bean gum is polydisperse consisting of non-ionic molecules.

Starch

Starch consists of two types of molecules, amylose (normally 20-30%) and amylopectin (normally 70-80%). Both consist of polymers of α-D-glucose units in the 4C1 conformation. In amylose these are linked-(1,4)-, with the ring oxygen atoms all on the same side, whereas in amylopectin about one residue in every twenty or so is also linked-(1,6)-forming branch-points. The relative proportions of amylose to amylopectin and-(1,6)-branch-points both depend on the source of the starch. The starch may derive from the source of corn (maize), wheat, potato, tapioca and rice. Amylopectin (without amylose) can be isolated from 'waxy' maize starch whereas amylose (without amylopectin) is best isolated after specifically hydrolyzing the amylopectin with pullulanase.

Amylose may form helix structures.

In one embodiment, the at least one hydrocolloid is a functional derivative of starch such as cross-linked, oxidized, acetylated, hydroxypropylated and partially hydrolyzed starch.

In a preferred embodiment, the adhesive comprises at least two hydrocolloids, wherein one hydrocolloid is gelatine and the at least one other hydrocolloid is selected from the group consisting of pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

In one embodiment, the adhesive comprises at least two hydrocolloids, wherein one hydrocolloid is gelatine and the at least other hydrocolloid is pectin.

In one embodiment, the adhesive comprises at least two hydrocolloids, wherein one hydrocolloid is gelatine and the at least other hydrocolloid is alginate.

In one embodiment, the adhesive comprises at least two hydrocolloids, wherein one hydrocolloid is gelatine and the at least other hydrocolloid is carboxymethylcellulose.

In a preferred embodiment, the adhesive according to the present invention comprises at least two hydrocolloids, wherein one hydrocolloid is gelatine and wherein the gelatine is present in the aqueous adhesive in an amount of 10 to 95 wt.-%, such as 20 to 80 wt.-%, such as 30 to 70 wt.-%, such as 40 to 60 wt.-%, based on the weight of the hydrocolloids.

In one embodiment, the adhesive comprises at least two hydrocolloids, wherein the one hydrocolloid and the at least other hydrocolloid have complementary charges.

In one embodiment, the one hydrocolloid is one or more of gelatine or gum arabic having complementary charges from one or more hydrocolloid(s) selected from the group of pectin, alginate, carrageenan, xanthan gum or carboxymethylcellulose.

In a preferred embodiment, the adhesive according to the present invention comprises at least two hydrocolloids, wherein one hydrocolloid is gelatine and wherein the gelatine is present in the aqueous adhesive in an amount of 10 to 95 wt.-%, such as 20 to 80 wt.-%, such as 30 to 70 wt.-%, such as 40 to 60 wt.-%, based on the weight of the hydrocolloids.

In one embodiment, the adhesive comprises at least two hydrocolloids, wherein the one hydrocolloid and the at least other hydrocolloid have complementary charges.

In one embodiment, the one hydrocolloid is one or more of gelatine or gum arabic having complementary charges from one or more hydrocolloid(s) selected from the group of pectin, alginate, carrageenan, xanthan gum or carboxymethylcellulose.

In one embodiment, the adhesive is capable of curing at a temperature of not more than 95° C., such as 5-95° C., such as 10-80° C., such as 20-60° C., such as 40-50° C.

The curing process may commence immediately after application of the adhesive to the fibres. The curing is defined as a process whereby the adhesive undergoes a physical and/or chemical reaction which in case of a chemical reaction usually increases the molecular weight of the compounds in the adhesive and thereby increases the viscosity of the adhesive, usually until the adhesive reaches a solid state.

In one embodiment the curing process comprises crosslinking and/or water inclusion as crystal water.

In one embodiment the cured adhesive contains crystal water that may decrease in content and raise in content depending on the prevailing conditions of temperature, pressure and humidity.

In one embodiment the curing process comprises a drying process.

In one embodiment the curing process comprises drying by pressure. The pressure may be applied by blowing air or gas through/over the mixture of mineral fibres and adhesive. The blowing process may be accompanied by heating or cooling or it may be at ambient temperature.

In one embodiment the curing process takes place in a humid environment.

The humid environment may have a relative humidity RH of 60-99%, such as 70-95%, such as 80-92%. The curing in a humid environment may be followed by curing or drying to obtain a state of the prevalent humidity.

In one embodiment the curing is performed in oxygen-depleted surroundings.

Without wanting to be bound by any particular theory, the applicant believes that performing the curing in an oxygen-depleted surrounding is particularly beneficial when the adhesive includes an enzyme because it increases the stability of the enzyme component in some embodiments, in particular of the transglutaminase enzyme, and thereby improves the crosslinking efficiency. In one embodiment, the curing process is therefore performed in an inert atmosphere, in particular in an atmosphere of an inert gas, like nitrogen.

In some embodiments, in particular in embodiments in which the adhesive includes phenolics, in particular tannins oxidizing agents can be added. Oxidising agents as additives can serve to increase the oxidising rate of the phenolics in particular tannins. One example is the enzyme tyrosinase which oxidizes phenols to hydroxy-phenols/quinones and therefore accelerates the adhesive forming reaction.

In another embodiment, the oxidising agent is oxygen, which is supplied to the adhesive. In one embodiment, the curing is performed in oxygen-enriched surroundings.

In one embodiment, the adhesive is not crosslinked.

In an alternative embodiment, the adhesive is crosslinked.

In one embodiment, the aqueous adhesive according to the present invention is not a thermoset adhesive.

A thermosetting composition is in a soft solid or viscous liquid state, preferably comprising a prepolymer, preferably comprising a resin that changes irreversibly into an infusible, insoluble polymer network by curing. Curing is typically induced by the action of heat, whereby typically temperatures above 95° C. are needed.

A cured thermosetting resin is called a thermoset or a thermosetting plastic/polymer—when used as the bulk material in a polymer composite, they are referred to as the thermoset polymer matrix.

In one embodiment, the aqueous adhesive according to the present invention does not contain a poly(meth)acrylic acid, a salt of a poly(meth)acrylic acid or an ester of a poly(meth)acrylic acid.

In one embodiment, the at least one hydrocolloid is a biopolymer or modified biopolymer.

Biopolymers are polymers produced by living organisms. Biopolymers may contain monomeric units that are covalently bonded to form larger structures.

There are three main classes of biopolymers, classified according to the monomeric units used and the structure of the biopolymer formed: Polynucleotides (RNA and DNA), which are long polymers composed of 13 or more nucleotide monomers; Polypeptides, such as proteins, which are polymers of amino acids; Polysaccharides, such as linearly bonded polymeric carbohydrate structures.

Polysaccharides may be linear or branched; they are typically joined with glycosidic bonds. In addition, many saccharide units can undergo various chemical modifications, and may form parts of other molecules, such as glycoproteins.

In one embodiment, the at least one hydrocolloid is a biopolymer or modified biopolymer with a polydispersity index regarding molecular mass distribution of 1, such as 0.9 to 1.

In one embodiment, the adhesive comprises proteins from animal sources, including collagen, gelatine and hydrolysed gelatine, and the adhesive further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the adhesive comprises proteins from animal sources, including collagen, gelatine and hydrolysed gelatine, and wherein the adhesive further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In a preferred embodiment, the adhesive according to the present invention is formaldehyde free.

For the purpose of the present application, the term "formaldehyde free" is defined to characterize a mineral wool product where the emission is below 5 µg/m$^2$/h of formaldehyde from the mineral wool product, preferably below 3 µg/m$^2$/h. Preferably, the test is carried out in accordance with ISO 16000 for testing aldehyde emissions.

A surprising advantage of embodiments of mineral wool products according to the present invention is that they show self-healing properties. After being exposed to very harsh conditions when mineral wool products loose a part of their strength, the mineral wool products according to the present invention can regain a part of, the whole of or even exceed the original strength. In one embodiment, the aged strength is at least 80%, such as at least 90%, such as at least 100%, such as at least 130%, such as at least 150% of the unaged strength. This is in contrast to conventional mineral wool products for which the loss of strength after being exposed to harsh environmental conditions is irreversible. While not wanting to be bound to any particular theory, the present inventors believe that this surprising property in mineral wool products according to the present invention is due to the complex nature of the bonds formed in the network of the cured adhesive, such as the protein crosslinked by the phenol and/or quinone containing compound or crosslinked by an enzyme, which also includes quaternary structures and hydrogen bonds and allows bonds in the network to be established after returning to normal environmental conditions. For an insulation product, which when e.g. used as a roof insulation can be exposed to very high temperatures in the summer, this is an important advantage for the long term stability of the product.

In one embodiment, the adhesive consists essentially of
at least one hydrocolloid;
optionally at least one oil;
optionally at least one pH-adjuster;
optionally at least one crosslinker;
optionally at least one anti-fouling agent;
optionally at least one anti-swelling agent;
water.

In one embodiment, the at least one oil is a non-emulsified hydrocarbon oil.

In one embodiment, the at least one oil is an emulsified hydrocarbon oil.

In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent is an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Natural antimicrobial agents may also be used, such as tannins, rosemary, and garlic essential oils, oregano, lemon grass, or cinnamon oil at different concentrations.

In one aspect of the invention, there is provided a mineral wool product comprising a multiple of lamellae, such as a sandwich panel core, said product comprising—a plurality of lamellae cut from a mineral wool web, and bonded together by applying an adhesive on the surfaces of two adjacent lamellae to form a web-like product, wherein the adhesive comprises at least one hydrocolloid.

In this aspect of the invention any of the features discussed above with respect to the adhesive may be applied.

The Adhesive Process

In one embodiment, after application of the adhesive the elements are subjected to pressure during bonding and preferably the total time for application of the adhesive and subjection to pressure is not more than 120 seconds, such as 60 seconds, such as 30 seconds, such as 20 seconds.

In one embodiment, the panels can be moved along stationary nozzles or stationary panels can be sprayed with the use of movable nozzles or applied with rollers. Spraying time and adhesive bonding time is 120 seconds maximum. Panels sprayed with the adhesive are pressed together.

In one embodiment, the adhesive can be applied to just one of the surfaces to be bonded but it may be applied to both.

In one embodiment, the protein component of the adhesive can be applied to a first surface to be bonded and the phenol and/or quinone containing compound and/or at least one enzyme can be applied to a second surface to be bonded and then the first and second surfaces are contacted with each other.

In one embodiment, the amount of cured adhesive is 10-1000 g/m² surface, such as 50-500 g/m² surface, such as 100-400 g/m² surface.

It is advantageous to achieve a balanced penetration of the adhesive into deeper layers of the element; such a connection would be more durable than a connection made by another method. Generally the adhesive does not penetrate more than 2 mm into the element.

In one embodiment, the adhesive is applied by means of a spraying, rolling, brushing, curtain painting, a sponge or a soft sponge roll.

EXAMPLES

In the following examples, several adhesives which fall under the definition of the present invention were prepared and compared to adhesives according to the prior art.

Adhesives According to the Prior Art

The following properties were determined for the adhesives according the prior art.

Reagents

Silane (Momentive VS-142) was supplied by Momentive and was calculated as 100% for simplicity. All other components were supplied in high purity by Sigma-Aldrich and were assumed anhydrous for simplicity unless stated otherwise.

Adhesive Component Solids Content—Definition

The content of each of the components in a given adhesive solution before curing is based on the anhydrous mass of the components. The following formula can be used:

$$\text{Binder component solids content (\%)} = \frac{\text{binder component } A \text{ solids (g)} + \text{binder component } B \text{ solids (g)} + \ldots}{\text{total weight of mixture (g)}} \times 100\%$$

Adhesive Solids—Definition and Procedure

The content of adhesive after curing is termed "adhesive solids".

Disc-shaped stone wool samples (diameter: 5 cm; height 1 cm) were cut out of stone wool and heat-treated at 580° C. for at least 30 minutes to remove all organics. The solids of the adhesive mixture (see below for mixing examples) were measured by distributing a sample of the adhesive mixture (approx. 2 g) onto a heat treated stone wool disc in a tin foil container. The weight of the tin foil container containing the stone wool disc was weighed before and directly after addition of the adhesive mixture. Two such adhesive mixture loaded stone wool discs in tin foil containers were produced and they were then heated at 200° C. for 1 hour. After cooling and storing at room temperature for 10 minutes, the samples were weighed and the adhesive solids were calculated as an average of the two results. A adhesive with the desired adhesive solids could then be produced by diluting with the required amount of water and 10% aq. silane (Momentive VS-142).

Reaction Loss—Definition

The reaction loss is defined as the difference between the adhesive component solids content and the adhesive solids.

Mechanical Strength Studies (Bar Tests)—Procedure

The mechanical strength of the adhesives was tested in a bar test. For each adhesive, 16 bars were manufactured from a mixture of the adhesive and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A 15% adhesive solids adhesive solution containing 0.5% silane (Momentive VS-142) of adhesive solids was obtained as described above under "adhesive solids". A sample of this adhesive solution (16.0 g) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). The mixtures placed in the slots were then pressed hard with a suitably sized flat metal bar to generate even bar surfaces. 16 bars from each adhesive were made in this fashion. The resulting bars were then cured at 200° C. for 1 h. After cooling to room temperature, the bars were carefully taken out of the containers. Eight of the 16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm²; support distance: 40 mm; max deflection 20 mm; nominal e-module 10000 N/mm²) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI\ (\%) = \frac{\text{Weight of bars before heat treatment (g)} - \text{Weight of bars after heat treatment (g)}}{\text{Weight of bars before heat treatment (g)}} \times 100\%$$

REFERENCE ADHESIVES FROM THE PRIOR ART PREPARED AS COMPARATIVE EXAMPLES

Adhesive Example, Reference Adhesive a (Phenol-Formaldehyde Resin Modified with Urea, a PUF-Resol)

A phenol-formaldehyde resin is prepared by reacting 37% aq. formaldehyde (606 g) and phenol (189 g) in the presence of 46% aq. potassium hydroxide (25.5 g) at a reaction temperature of 84° C. preceded by a heating rate of approximately 1° C. per minute. The reaction is continued at 84° C. until the acid tolerance of the resin is 4 and most of the phenol is converted. Urea (241 g) is then added and the mixture is cooled.

The acid tolerance (AT) expresses the number of times a given volume of a adhesive can be diluted with acid without the mixture becoming cloudy (the adhesive precipitates). Sulfuric acid is used to determine the stop criterion in a adhesive production and an acid tolerance lower than 4 indicates the end of the adhesive reaction. To measure the AT, a titrant is produced from diluting 2.5 mL conc. sulfuric acid (>99%) with 1 L ion exchanged water. 5 mL of the adhesive to be investigated is then titrated at room temperature with this titrant while keeping the adhesive in motion by manually shaking it; if preferred, use a magnetic stirrer and a magnetic stick. Titration is continued until a slight cloud appears in the adhesive, which does not disappear when the adhesive is shaken.

The acid tolerance (AT) is calculated by dividing the amount of acid used for the titration (mL) with the amount of sample (mL):

$AT$=(Used titration volume (mL))/(Sample volume (mL))

Using the urea-modified phenol-formaldehyde resin obtained, a adhesive is made by addition of 25% aq. ammonia (90 mL) and ammonium sulfate (13.2 g) followed by water (1.30 kg). The adhesive solids were then measured as described above and the mixture was diluted with the required amount of water and silane (Momentive VS-142) for mechanical strength studies (15% adhesive solids solution, 0.5% silane of adhesive solids).

Adhesives According to the Present Invention

The following properties were determined for the adhesives according the present invention.

Reagents

Gelatines (Speisegelatine, type A, porcine, 120 and 180 bloom; Imagel LB, type B, 122 bloom) were obtained from Gelita AG. Tannorouge chestnut tree tannin was obtained from Brouwland bvba. Agar agar (05039), gellan gum (P8169), pectin from citrus peel (P9135), sodium alginate from brown algae (A0682), sodium carboxymethyl cellulose (419303), soluble starch (S9765), and sodium hydroxide were obtained from Sigma-Aldrich. For simplicity, these reagents were considered completely pure and anhydrous.

Adhesive Component Solids Content—Definition

The content of each of the components in a given adhesive solution before curing is based on the anhydrous mass of the components. The following formula can be used:

$$\text{Binder component solids content (\%)} = \frac{\text{binder component } A \text{ solids (g)} + \text{binder component } B \text{ solids (g)} + \ldots}{\text{total weight of mixture (g)}} \times 100\%$$

Mechanical Strength Studies (Bar Tests)—Procedure

The mechanical strength of the adhesives was tested in a bar test. For each adhesive, 8-16 bars were manufactured from a mixture of the adhesive and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A adhesive solution was obtained as described in the examples below. For comparatively slower setting adhesives, a sample of the adhesive solution (16.0 g for adhesives with 10-15% adhesive component solids; 32.0 g for adhesives with 5% adhesive component solids) was mixed well with shots (80.0 g). The resulting mixture was then divided evenly into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). For comparatively faster setting adhesives, a sample of the adhesive solution (8.0 g for adhesives with 10-15% adhesive component solids and 16.0 g for adhesives with 5% adhesive component solids) was mixed well with shots (40.0 g, pre-heated to 35-40° C. before use), and the resulting mixture was then divided evenly into two slots only. During the manufacture of each bar, the mixtures placed in the slots were pressed as required and then evened out with a plastic spatula to generate an even bar surface. 8-16 bars from each adhesive were made in this fashion. The resulting bars were then cured at room temperature for 1-2 days or first cured for 15 minutes in an oven at the temperatures listed in the tables followed by curing for 1-2 days at room temperature. If still not sufficiently cured after that time, the bars were cured for 1 day at 35° C. The bars were then carefully taken out of the containers, turned upside down and left for a day at room temperature to cure completely. Half of the 8-16 bars were aged in an autoclave (15 min/120° C./1.2 bar).

After drying for 1-2 days, all bars were then broken in a 3 point bending test (test speed: 10.0 mm/min; rupture level: 50%; nominal strength: 30 N/mm$^2$; support distance: 40 mm; max deflection 20 mm; nominal e-module 10000 N/mm$^2$) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI\ (\%) = \frac{\text{Weight of bars before heat treatment (g)} - \text{Weight of bars after heat treatment (g)}}{\text{Weight of bars before heat treatment (g)}} \times 100\%$$

Adhesives According to the Present Invention

Adhesive Example, Entry 1

A mixture of gelatine (Speisegelatine, type A, porcine, 120 bloom, 7.5 g) in water (42.5 g) was stirred at 50° C. for approx. 15-30 min until a clear solution was obtained (pH 5.1). The resulting solution was then used in the subsequent experiments.

Adhesive Example, Entry 3

A mixture of gelatine (Speisegelatine, type A, porcine, 180 bloom, 8.82 g) in water (50.0 g) was stirred at 50° C. for approx. 15-30 min until a clear solution was obtained (pH 5.2). The resulting solution was then used in the subsequent experiments.

Adhesive Example, Entry 5

A mixture of gelatine (Imagel LB, type B, 122 bloom, 8.82 g) in water (50.0 g) was stirred at 50° C. for approx. 15-30 min until a clear solution was obtained (pH 5.1). The resulting solution was then used in the subsequent experiments.

Adhesive Example, Entry 7

To water (50.0 g) stirred vigorously at 85° C. was added sodium carboxymethyl cellulose (2.63 g) portion-wise over approx. 15 minutes. Stirring was continued for 0.5-1 h further at 85° C. until a clear solution was obtained (pH 8.4). The resulting solution was then used in the subsequent experiments.

Adhesive Example, Entry 8

To water (50.0 g) stirred vigorously at 85° C. was added soluble starch (2.63 g) portion-wise over approx. 15 minutes. Stirring was continued for 0.5-1 h further at 85° C. until a clear solution was obtained (pH 6.4). The resulting solution was then used in the subsequent experiments.

Adhesive Example, Entry 9

To water (50.0 g) stirred vigorously at 85° C. was added agar agar (2.63 g) portion-wise over approx. 15 minutes. Stirring was continued for 0.5-1 h further at 85° C. until a clear solution was obtained.
A mixture of gelatine (Speisegelatine, type A, porcine, 120 bloom, 8.82 g) in water (50.0 g) was stirred at 50° C. for approx. 15-30 min until a clear solution was obtained. A portion of the above agar agar solution (19.6 g, thus efficiently 0.98 g agar agar and 18.6 g water) was then added and stirring was continued at 50° C. for 5 min further (pH 5.3). The resulting solution was then used in the subsequent experiments.

Adhesive Example, Entry 10

To water (50.0 g) stirred vigorously at 85° C. was added gellan gum (2.63 g) portion-wise over approx. 15 minutes. Stirring was continued for 0.5-1 h further at 85° C. until a clear solution was obtained.
A mixture of gelatine (Speisegelatine, type A, porcine, 120 bloom, 8.82 g) in water (50.0 g) was stirred at 50° C. for approx. 15-30 min until a clear solution was obtained. A portion of the above gellan gum solution (19.6 g, thus efficiently 0.98 g gellan gum and 18.6 g water) was then added and stirring was continued at 50° C. for 5 min further (pH 5.3). The resulting solution was then used in the subsequent experiments.

Adhesive Example, Entry 11

To water (50.0 g) stirred vigorously at 85° C. was added pectin (2.63 g) portion-wise over approx. 15 minutes. Stirring was continued for 0.5-1 h further at 85° C. until a clear solution was obtained.
A mixture of gelatine (Speisegelatine, type A, porcine, 120 bloom, 8.82 g) in water (50.0 g) was stirred at 50° C. for approx. 15-30 min until a clear solution was obtained. A portion of the above pectin solution (19.6 g, thus efficiently 0.98 g pectin and 18.6 g water) was then added and stirring was continued at 50° C. for 5 min further (pH 4.8). The resulting solution was then used in the subsequent experiments.

Adhesive Example, Entry 12

To water (50.0 g) stirred vigorously at 85° C. was added sodium alginate (2.63 g) portion-wise over approx. 15 minutes. Stirring was continued for 0.5-1 h further at 85° C. until a clear solution was obtained.
A mixture of gelatine (Speisegelatine, type A, porcine, 120 bloom, 8.82 g) in water (50.0 g) was stirred at 50° C. for approx. 15-30 min until a clear solution was obtained. A portion of the above sodium alginate solution (19.6 g, thus efficiently 0.98 g sodium alginate and 18.6 g water) was then added and stirring was continued at 50° C. for 5 min further (pH 5.3). The resulting solution was then used in the subsequent experiments.

Adhesive Example, Entry 13

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 8.00 g) in water (72.0 g) was stirred at 50° C. for approx. 15-30 min until a clear solution was obtained (pH 4.8). 1M NaOH (3.50 g) was then added (pH 9.3) followed by a portion of the above chestnut tree tannin solution (3.60 g; thus efficiently 0.80 g chestnut tree tannin). After stirring for 1-2 minutes further at 50° C., the resulting brown mixture (pH 9.2) was used in the subsequent experiments.

Adhesive Example, Entry 14

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.9). 1M NaOH (4.00 g) was then added (pH 9.1) followed by a portion of the above chestnut tree tannin solution (4.50 g; thus efficiently 1.00 g chestnut tree tannin). After stirring for 1-2 minutes further at 50° C., the resulting brown mixture (pH 9.1) was used in the subsequent experiments.

Adhesive Example, Entry 17

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 180 bloom, 10.0 g) in water (56.7 g) was stirred at 50° C. for approx. 15-30 min until a clear solution was obtained (pH 4.8). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Adhesive Example, Entry 19

To 1M NaOH (15.75 g) stirred at room temperature was added chestnut tree tannin (4.50 g). Stirring was continued at room temperature for 5-10 min further, yielding a deep red-brown solution.

A mixture of gelatine (Imagel LB, type B, 122 bloom, 10.0 g) in water (56.7 g) was stirred at 50° C. for approx. 15-30 min until a clear solution was obtained (pH 4.7). 1M NaOH (3.50 g) was then added (pH 9.2) followed by a portion of the above chestnut tree tannin solution (4.50 g; thus efficiently 1.00 g chestnut tree tannin). After stirring for 1-2 minutes further at 50° C., the resulting brown mixture (pH 9.2) was used in the subsequent experiments.

Adhesive Example, Entry 21

To water (50.0 g) stirred vigorously at 85° C. was added agar agar (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.1) followed by a portion of the above chestnut tree tannin solution (4.50 g; thus efficiently 1.00 g chestnut tree tannin) and then a portion of the above agar agar solution (20.0 g; thus efficiently 1.00 g agar agar). After stirring for 1-2 minutes further at 50° C., the resulting brown mixture (pH 8.8) was used in the subsequent experiments.

Adhesive Example, Entry 22

To water (50.0 g) stirred vigorously at 85° C. was added pectin (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.50 g) was then added (pH 9.6) followed by a portion of the above chestnut tree tannin solution (4.50 g; thus efficiently 1.00 g chestnut tree tannin) and then a portion of the above pectin solution (20.0 g; thus efficiently 1.00 g pectin). After stirring for 1-2 minutes further at 50° C., the resulting brown mixture (pH 8.9) was used in the subsequent experiments.

Adhesive Example, Entry 23

To water (50.0 g) stirred vigorously at 85° C. was added sodium alginate (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.6). 1M NaOH (4.00 g) was then added (pH 9.2) followed by a portion of the above chestnut tree tannin solution (4.50 g; thus efficiently 1.00 g chestnut tree tannin) and then a portion of the above sodium alginate solution (20.0 g; thus efficiently 1.00 g sodium alginate). After stirring for 1-2 minutes further at 50° C., the resulting brown mixture (pH 9.0) was used in the subsequent experiments.

Adhesive Example, Entry 24

To water (50.0 g) stirred vigorously at 85° C. was added soluble starch (2.63 g) portion-wise over approx. 15 minutes. Stirring was continued for 0.5-1 h further at 85° C. until a clear solution was obtained.

To 1M NaOH (15.75 g) stirred at room temperature was added chestnut tree tannin (4.50 g). Stirring was continued at room temperature for 5-10 min further, yielding a deep red-brown solution.

A mixture of gelatine (Speisegelatine, type A, porcine, 120 bloom, 10.0 g) in water (56.7 g) was stirred at 50° C. for approx. 15-30 min until a clear solution was obtained (pH 4.8). 1M NaOH (4.00 g) was then added (pH 9.1) followed by a portion of the above chestnut tree tannin solution (4.50 g; thus efficiently 1.00 g chestnut tree tannin) and then a portion of the above soluble starch solution (20.0 g; thus efficiently 1.00 g soluble starch). After stirring for 1-2 minutes further at 50° C., the resulting brown mixture (pH 8.8) was used in the subsequent experiments.

TABLE 1-1

| Reference adhesive | |
|---|---|
| Example | A |
| Adhesive properties | |
| Adhesive solids (%) | 15.0 |
| Reaction loss (%) | 28.5 |
| pH | 9.6 |
| Bar curing conditions | |
| Temperature (° C./1 h) | 200 |
| Bar properties | |
| Mechanical strength, unaged (kN) | 0.39 |
| Mechanical strength, aged (kN) | 0.28 |
| LOI, unaged (%) | 2.8 |

TABLE 1-2

| | Various hydrocolloids | | | | | | | | | | | |
|---|---|---|---|---|---|---|---|---|---|---|---|---|
| Example | 1 | 2 | 3 | 4 | 5 | 6 | 7 | 8 | 9 | 10 | 11 | 12 |
| Adhesive Hydrocolloid (%-wt.) | | | | | | | | | | | | |
| Gelatine, Speisegelatine, 120 bloom | 100 | 100 | — | — | — | — | — | — | 90 | 90 | 90 | 90 |
| Gelatine, Speisegelatine, 180 bloom | — | — | 100 | 100 | — | — | — | — | — | — | — | — |
| Gelatine, Imagel LB, 122 bloom | — | — | — | — | 100 | 100 | — | — | — | — | — | — |
| Agar agar | — | — | — | — | — | — | — | — | 10 | — | — | — |
| Gellan gum | — | — | — | — | — | — | — | — | — | 10 | — | — |
| Pectin | — | — | — | — | — | — | — | — | — | — | 10 | 10 |
| Sodium alginate | — | — | — | — | — | — | — | — | — | — | — | — |
| Sodium carboxymethyl cellulose | — | — | — | — | — | — | 100 | — | — | — | — | — |
| Soluble starch | — | — | — | — | — | — | — | 100 | — | — | — | — |
| Crosslinker (%-wt.) [a] | | | | | | | | | | | | |
| Chestnut tree tannin | — | — | — | — | — | — | — | — | — | — | — | — |
| Base (%-wt.) [b] | | | | | | | | | | | | |
| Sodium hydroxide | — | — | — | — | — | — | — | — | — | — | — | — |
| Adhesive mixing and bar manufacture | | | | | | | | | | | | |
| Mixing temperature (° C.) | 50 | 50 | 50 | 50 | 50 | 50 | 85 | 85 | 50/85 | 50/85 | 50/85 | 50/85 |
| Adhesive component solids content (%) | 15.0 | 10.0 | 15.0 | 10.0 | 15.0 | 10.0 | 5.0 | 5.0 | 12.5 | 12.5 | 12.5 | 12.5 |
| pH | 5.1 | 4.9 | 5.2 | 4.9 | 5.1 | 5.0 | 8.4 | 6.4 | 5.3 | 5.3 | 4.8 | 5.3 |
| Pre-heated shots (35-40° C.) | — | — | — | Yes | — | — | — | — | — | — | — | — |
| Curing Temperature (° C./15 min to rt) | rt | rt | rt | rt | rt | rt | rt | rt | rt | rt | rt | rt |
| Bar properties | | | | | | | | | | | | |
| Mechanical strength, unaged (kN) | 0.31 | 0.24 | 0.28 | 0.13 | 0.20 | 0.13 | 0.13 | 0.11 | 0.11 | 0.09 | 0.13 | 0.13 |
| Mechanical strength, aged (kN) | 0.30 | 0.28 | 0.27 | 0.17 | 0.22 | 0.15 | 0.15 | 0.12 | 0.15 | 0.11 | 0.14 | 0.22 |
| LOI, unaged (%) | 2.9 | 1.9 | 2.9 | 1.9 | 2.8 | 1.9 | 1.9 | 2.0 | 2.4 | 2.5 | 2.4 | 2.3 |

[a] Of hydrocolloid(s).
[b] Of hydrocolloid(s) + crosslinker.

TABLE 1-3

| | Various hydrocolloids, crosslinkers | | | | | | | | | | | |
|---|---|---|---|---|---|---|---|---|---|---|---|---|
| Example | 13 | 14 | 15 | 16 | 17 | 18 | 19 | 20 | 21 | 22 | 23 | 24 |
| Adhesive Polyelectrolytic hydrocolloid (%-wt.) | | | | | | | | | | | | |
| Gelatine, Speisegelatine, 120 bloom | 100 | 100 | 100 | 100 | — | — | — | — | 91 | 91 | 91 | 91 |
| Gelatine, Speisegelatine, 180 bloom | — | — | — | — | 100 | 100 | — | — | — | — | — | — |
| Gelatine, Imagel LB, 122 bloom | — | — | — | — | — | — | 100 | 100 | — | — | — | — |
| Agar agar | — | — | — | — | — | — | — | — | 9 | — | — | — |
| Gellan gum | — | — | — | — | — | — | — | — | — | — | — | — |
| Pectin | — | — | — | — | — | — | — | — | — | 9 | — | — |
| Sodium alginate | — | — | — | — | — | — | — | — | — | — | 9 | — |

TABLE 1-3-continued

Various hydrocolloids, crosslinkers

| Example | 13 | 14 | 15 | 16 | 17 | 18 | 19 | 20 | 21 | 22 | 23 | 24 |
|---|---|---|---|---|---|---|---|---|---|---|---|---|
| Sodium carboxymethyl cellulose | — | — | — | — | — | — | — | — | — | — | — | — |
| Soluble starch | — | — | — | — | — | — | — | — | — | — | — | 9 |
| Crosslinker (%-wt.) [a] | | | | | | | | | | | | |
| Chestnut tree tannin | 10 | 10 | 10 | 10 | 10 | 10 | 10 | 10 | 9 | 9 | 9 | 9 |
| Base (%-wt.) [b] | | | | | | | | | | | | |
| Sodium hydroxide | 2.7 | 2.6 | 2.6 | 2.6 | 2.4 | 2.4 | 2.4 | 2.4 | 2.4 | 2.5 | 2.4 | 2.4 |
| Adhesive mixing and bar manufacture | | | | | | | | | | | | |
| Mixing temperature (° C.) | 50 | 50 | 50 | 50 | 50 | 50 | 50 | 50 | 50/85 | 50/85 | 50/85 | 50/85 |
| Adhesive component solids content (%) | 10.4 | 15.0 | 15.0 | 15.0 | 15.1 | 15.1 | 15.1 | 15.1 | 12.9 | 12.9 | 12.9 | 12.9 |
| pH | 9.2 | 9.1 | 9.1 | 9.1 | 9.2 | 9.2 | 9.2 | 9.2 | 8.8 | 8.9 | 9.0 | 8.8 |
| Pre-heated shots (35-40° C.) | — | — | — | — | Yes | Yes | — | — | — | — | — | — |
| Curing Temperature (° C./15 min to rt) | rt | rt | 35 | 55 | 35 | 55 | 35 | 55 | rt | rt | rt | rt |
| Bar properties | | | | | | | | | | | | |
| Mechanical strength, unaged (kN) | 0.16 | 0.23 | 0.26 | 0.27 | 0.30 | 0.27 | 0.25 | 0.27 | 0.16 | 0.18 | 0.17 | 0.18 |
| Mechanical strength, aged (kN) | 0.15 | 0.21 | 0.25 | 0.25 | 0.25 | 0.31 | 0.27 | 0.26 | 0.15 | 0.13 | 0.15 | 0.18 |
| LOI, unaged (%) | 1.9 | 2.7 | 2.7 | 2.7 | 2.7 | 2.8 | 2.8 | 2.8 | 2.4 | 2.6 | 2.4 | 2.4 |

[a] Of hydrocolloid(s).
[b] Of hydrocolloid(s) + crosslinker

As can be seen from comparing the results in Table 1.1 with Tables 1.2 and 1.3, the adhesives used in the present invention require lower temperatures for curing. The reference adhesive requires temperatures of 200° C. for curing, while adhesives 1 to 24 cure at 55° C. and below, typically at ambient temperature. This means that the adhesives of the present invention are capable of being cured on-site or at the manufacturing or process stage.

The invention claimed is:

1. A method of producing a mineral wool product comprising a multiple of lamellae, said method comprising the steps of:
   providing a cured mineral wool web;
   cutting said mineral wool web longitudinally into a plurality of lamellae;
   turning each of the plurality of lamellae 90° about their longitudinal axis;
   bonding the lamellae in the turned orientation together by an adhesive on surfaces of two adjacent of the plurality of turned lamellae; and
   curing the adhesive, the step of curing comprising a drying process involving blowing air or gas through the mineral wool product, the step of curing being carried out at temperatures from 5 to 95° C., wherein the adhesive comprises at least one hydrocolloid,
   wherein the adhesive comprises:
   proteins from animal sources, and the adhesive further comprises at least one phenol containing compound, wherein the at least one phenol containing compound is tannin selected from one or more components from the group consisting of tannic acid, condensed tannins (proanthocyanidins), hydrolysable tannins, gallotannins, ellagitannins, complex tannins, and tannin originating from one or more of oak, chestnut, staghorn sumac and fringe cups, and/or
   proteins from animal sources, and wherein the adhesive further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), lysyl oxidase (EC 1.4.3.13), and peroxidase (EC 1.11.1.7);
   and a density of the mineral wool product being in the range of 50-300 kg/m3.

2. The method according to claim 1, further comprising applying the adhesive to a surface of the cured mineral wool web before cutting the mineral wool web into lamellae.

3. The method according to claim 1, wherein the at least one hydrocolloid is selected from the group consisting of gelatine, pectin, starch, alginate, agar, carrageenan, gellan gum, guar gum, gum arabic, locust bean gum, xanthan gum, and cellulose derivatives.

4. The method according to claim 1, wherein the at least one hydrocolloid is a polyelectrolytic hydrocolloid.

5. The method according to claim 1, wherein the at least one hydrocolloid is selected from the group consisting of gelatine, pectin, alginate, carrageenan, gum arabic, xanthan gum, and cellulose derivatives.

6. The method according to claim 1, wherein at least one hydrocolloid of the adhesive comprises at least two hydrocolloids, wherein one hydrocolloid is gelatine and the at least one other hydrocolloid is selected from the group consisting of pectin, starch, alginate, agar, carrageenan, gellan gum, guar gum, gum arabic, locust bean gum, xanthan gum, and cellulose derivatives.

7. The method according to claim 6, wherein the gelatine is present in the adhesive in an amount of 10 to 95 wt. % based on the weight of the hydrocolloids.

8. The method according to claim 6, wherein the one hydrocolloid and the at least other hydrocolloid have complementary charges.

9. The method according to claim 1, wherein the adhesive is not a thermoset adhesive.

10. The method according to claim 1, wherein the adhesive does not contain a poly(meth)acrylic acid, a salt of a poly(meth)acrylic acid or an ester of a poly(meth)acrylic acid.

11. The method according to claim 1, wherein the at least one hydrocolloid is a biopolymer or modified biopolymer.

12. The method according to claim 1, wherein the adhesive is formaldehyde-free.

13. The method according to claim 1, wherein the adhesive further comprises
  at least one of
  at least one oil,
  at least one pH-adjuster,
  at least one crosslinker,
  at least one anti-fouling agent,
  at least one anti-swelling agent, and
  water.

14. The method according to claim 1, wherein the mineral wool product is a sandwich panel core.

15. The method according to claim 1, wherein the adhesive corresponds with a binder in the mineral wool product.

16. The method according to claim 1, wherein the step of curing comprising a drying process further comprises increasing temperature.

17. The method according to claim 1, wherein a main fibre orientation of the mineral wool is substantially in a plane perpendicular to surfaces of the mineral wool product after the bonding.

18. The method according to claim 1, wherein the density of the mineral wool product is in the range of 50-200 kg/m3.

19. The method according to claim 1, wherein the proteins from animal sources include collagen, gelatine and hydrolysed gelatine.

20. The method according to claim 1, wherein the polyphenol oxidase (EC 1.14.18.1) is catechol oxidase, tyrosine oxidase and phenoloxidase.

21. The method according to claim 3, wherein the cellulose derivatives is carboxymethylcellulose, arabinoxylan, cellulose, curdlan, or β-glucan.

22. The method according to claim 5, wherein the cellulose derivatives is carboxymethylcellulose.

23. The method according to claim 6, wherein the cellulose derivatives is carboxymethylcellulose, arabinoxylan, cellulose, curdlan, or β-glucan.

24. The method according to claim 1, wherein the adhesive is cured in the bonding step in not more than 120 seconds.

25. The method of claim 1, wherein the step of curing is carried out at temperatures from 10 to 80° C.

26. The method of claim 1, wherein the step of curing is carried out at temperatures from 20 to 60° C.

27. The method of claim 1, wherein the step of curing is carried out at temperatures from 40 to 50° C.

28. The method according to claim 6, wherein the gelatine is present in the adhesive in an amount of 20 to 80 wt. % based on the weight of the hydrocolloids.

29. The method according to claim 6, wherein the gelatine is present in the adhesive in an amount of 30 to 70 wt. % based on the weight of the hydrocolloids.

30. The method according to claim 6, wherein the gelatine is present in the adhesive in an amount of 40 to 60 wt. % based on the weight of the hydrocolloids.

31. The method according to claim 1, wherein the density of the mineral wool product is in the range of 65-100 kg/m3.

* * * * *